United States Patent [19]

Charvin

[11] Patent Number: 4,850,954
[45] Date of Patent: Jul. 25, 1989

[54] CONNECTING DEVICE FOR AN EXTRACORPOREAL CIRCULATION CIRCUIT

[76] Inventor: Guy Charvin, 25 Chemin de la Peyrigoue Parc St-Honoré, 06600 Antibes, France

[21] Appl. No.: 907,841

[22] Filed: Sep. 15, 1986

[30] Foreign Application Priority Data

Sep. 16, 1985 [FR] France ............................ 85 13703

[51] Int. Cl.⁴ .................................. A61M 37/00
[52] U.S. Cl. ................... 604/4; 128/DIG. 3; 206/438; 604/280; 604/283
[58] Field of Search .............. 604/4, 8, 9, 29, 175, 604/905, 264, 280, 283, 284, 272, 5–7, 281, 282; 128/DIG. 3, 348.1; 206/69, 438, 439, 443; 422/44–48

[56] References Cited

U.S. PATENT DOCUMENTS

| | | | |
|---|---|---|---|
| 2,702,034 | 2/1955 | Walter | 206/438 |
| 2,935,068 | 5/1960 | Donaldson | 604/8 |
| 3,626,938 | 12/1971 | Versaci | 604/122 |
| 3,851,814 | 12/1974 | Stage | 206/439 |
| 3,853,126 | 12/1974 | Schulte | 604/8 |
| 3,877,843 | 4/1975 | Fischel | 128/DIG. 3 |
| 4,216,860 | 8/1980 | Heimann | |
| 4,423,732 | 1/1984 | Tarjan et al. | 206/438 |
| 4,540,399 | 9/1985 | Litzie et al. | 604/4 |
| 4,588,085 | 5/1986 | Sussman | 604/9 |

FOREIGN PATENT DOCUMENTS

| | | |
|---|---|---|
| 0130315 | 1/1985 | European Pat. Off. |
| 1566619 | 12/1970 | Fed. Rep. of Germany |
| 1545979 | 11/1968 | France ............ 604/4 |

*Primary Examiner*—C. Fred Rosenbaum
*Assistant Examiner*—Mario Costantino
*Attorney, Agent, or Firm*—Fay, Sharpe, Beall, Fagan, Minnich & McKee

[57] ABSTRACT

Device for extracorporeal circulation (E.C.C.) circuit, includes tubes known as lines which are intended to be used during a surgical operation requiring the extracorporeal oxygenation of the blood. In this device, are provided an arterial line and a venous line whose linkage with each other and in a closed circuit to the heart-lung machine forms the arteriovenous shunt, the linkage of the distal ends of the arterial line (1) and the venous line (2) is accomplished through at least one arterial cannula (3) connected detachably at its distal end to the venous line (2).

14 Claims, 2 Drawing Sheets

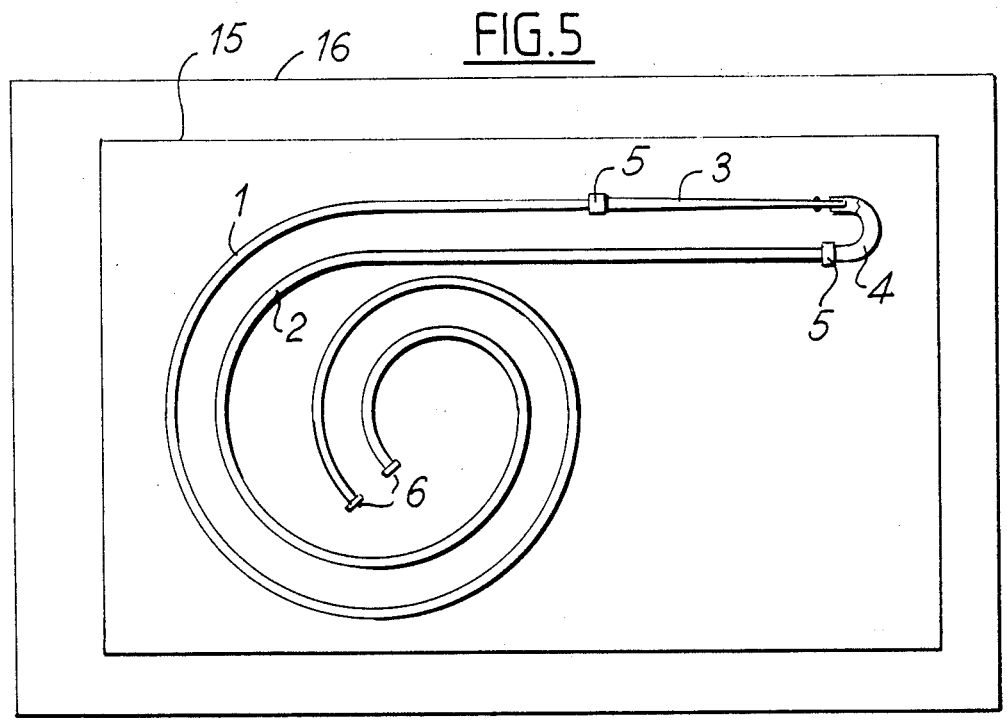
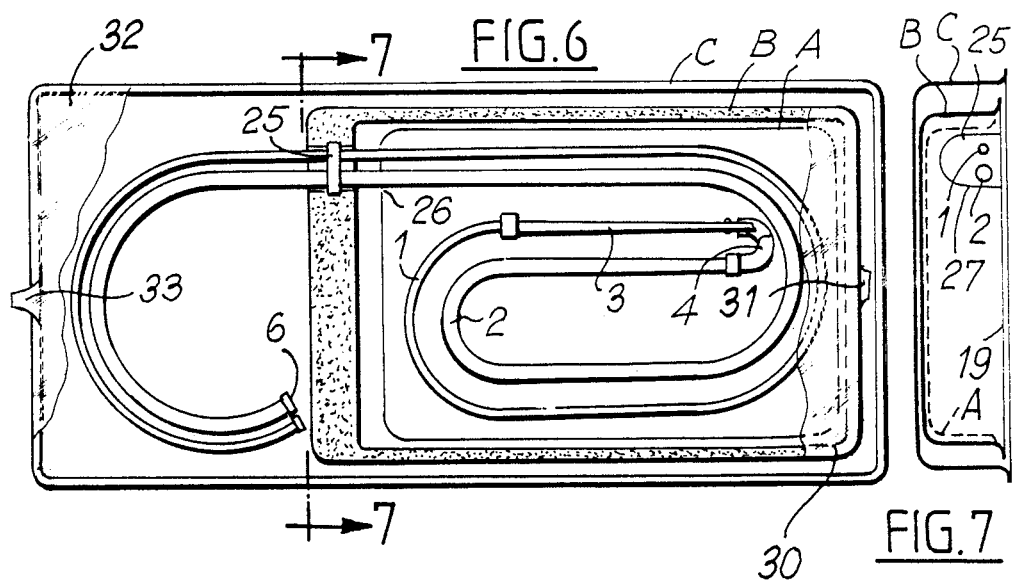

CONNECTING DEVICE FOR AN EXTRACORPOREAL CIRCULATION CIRCUIT

The present invention relates to extracorporeal circulation (E.C.C.) circuits which provide for the linkage, via a connecting device composed essentially of tubes and their accessories—known as lines, in the technical jargon—between a patient and a heart-lung machine during a surgical operation requiring the extracorporeal oxygenation of the blood.

This device comprises the essential lines, known as the arterial line and the venous line, and auxiliary lines such as suction lines, cardioplegia line, left discharge line, which are traditionally presented, separately, or completely or partially grouped together, in a sterile packing. Immediately before the patient is installed in extracorporeal circulation, this packing for protecting the sterility is opened and the surgeon or his operating assistant passes the extracorporeal circulation technician the ends of the lines which have to be connected to the heart-lung oxygenation machine. There then follows, in particular, the filling of the arterial line and the venous line, both being connected in a closed circuit to form what is commonly known as an arteriovenous shunt, by means of a liquid such as a solution, supplementary blood, and the like. It is then necessary to ensure the complete removal of the air bubbles formed during the phase of filling this shunt. Only after this phase of bubble removal can the surgeon, after splitting the arteriovenous shunt, connect at least one arterial cannula to the free end of the arterial line and/or one or more venous cannula or cannulae to the free end of the venous line. It is then appropriate to carry out the filling of the cannulae and the removal of bubbles therefrom.

The filling of any intravascular cannula is traditionally performed, starting with an unattached cannula, by introducing its distal end into the appropriate vessel of the patient: under the effect of its pressure, the blood fills the cannula to its proximal seating.

The removal of bubbles from the said cannula is then performed at its proximal seating, by various devices or means which remove any residual air from the cannula and prevent the introduction of external air at the precise instant that the cannula is connected to its extracorporeal line.

Similarly, there are devices which, after this connecting operation, enable any residual air inopportunely trapped in the closed circuit to be removed.

From the practical standpoint, these conventional operations of filling cannulae, connection and bubble removal are tedious and awkward, and require the use of different accessories. In effect, when the surgeon splits the arteriovenous shunt to release the distal ends of the arterial line and venous line, each of these lines must be clamped beforehand to avoid any outflow of the filling liquid. Similarly, after introduction of the intravascular cannula into the vessel and the filling thereof, the surgeon has to clamp its proximal end to prevent blood from escaping to the outside. Lastly, he has to connect each cannula to the distal end of the corresponding line taking care not to trap air inside the circuit. One of the means traditionally used for preventing the entry of air into the circuit when the cannula is connected to its line consists in directing a liquid (such as a sterile solution) at the same time onto the orifice of the proximal seating of the cannula and onto the distal orifice of the line at the precise instant that the cannula is connected to the line, so that there is a simultaneous overflow of liquid at both of these orifices, and in preventing air from being trapped during the connection. One of the means traditionally used for removing air bubbles inopportunely trapped after the cannula/line connection operation consists in using a cannula/line linking connector which possesses at the side an opening in the form of a female Luer cone seating to which the surgeon may connect a syringe enabling the residual air bubbles to be sucked out. Once this operation has been completed, the surgeon will seal this female seating using a lockable plug having a male luer cone.

It should be noted that the operation of bubble removal from the arterial cannula is fraught with far more consequences than that of bubble removal from the venous cannula. In effect, for the latter, the presence of residual air bubbles does not have major consequences since the venous blood leaves the patient and travels to the artificial oxygenator and its downstream devices for trapping air bubbles. In contrast, the removal of bubbles from the arterial cannula and the connection of its proximal seating to the distal end of the arterial line are difficult and risky operations: it is imperative that there is no air bubble in this portion of the circuit since the filling liquid initially present in the arterial line and the arterial blood initially present in the arterial cannula will both be propelled, under the action of the extracorporeal circulation pump, directly into the patient's artery (generally the aorta).

Moreover, it is extremely important that the arterial and venous cannulae should be altogether securely united with their lines: in particular, the proximal seating of the arterial cannula must be especially firmly attached to the distal end of the arterial line on account of the pressure generated by the pump. To provide for firm attachment, the surgeon generally uses special links, tightened by means of a suitable clip, enabling the cannulae to be clamped on the distal connectors of the lines. This operation, of course, requires additional time and is sometimes awkward.

In summary, the equipment for traditional distal circuits—isolated cannulae, simple arteriovenous shunt, connectors and syringes for bubble removal, multiple clamps, links, clips, and the like—requires manipulations which substantially prolong the operating time and which, in addition, involves the not insignificant risk of introducing air into the vascular system (as a result of poor bubble removal) or risks of subsequent disconnection of a cannula during extracorporeal circulation (as a result of a hasty connection of the cannula at the time of use to the distal end of its line).

It is the intention of the invention to remedy all these disadvantages. To this end, its subject is a connecting device for an extracorporeal circulation circuit comprising an arterial line and a venous line whose linkage with each other and in a closed circuit to the heart-lung machine forms the arteriovenous shunt, characterized in that linkage of the distal ends of the arterial line and the venous line is accomplished through at least one arterial cannula connected detachably at its distal end to the venous line.

This detachable linkage can be provided by a U- or V-shaped hollow elastic sleeve engaged at one end on the arterial cannula and at its other end, directly or via a connector, on the venous line or alternatively on the distal end of a venous cannula attached at its proximal end to the venous line.

It is, in effect, possible to mount, according to the invention in the arteriovenous shunt, not only the arterial cannula or cannulae, but also the venous cannula or cannulae. When two venous cannulae are provided in this manner, the linking member, instead of being a simple sleeve, is a three-entry linkage, two of the entries being intended to be engaged on the venous cannulae. As a variant, the two venous cannulae are not incorporated in the arteriovenous shunt, but the latter contains a three-entry connector, one of the entries being engaged in the distal end of the venous line and the other two engaged in the two remaining entries of the connecting member and ready to receive two venous cannulae after removal of this member.

When there are two arterial cannulae and one venous cannula, the connecting member is a three-entry sleeve. Lastly, when there are two arterial cannulae and two venous cannulae, the connecting member is a four-entry sleeve or, according to another embodiment, there are two one-way sleeves each connecting the distal end of an arterial cannula to the proximal end of a venous cannula or its connector.

This improved connecting device enables the arterial and venous lines and the arterial cannula or cannulae (and, where appropriate, the venous cannula or cannulae) to be filled simultaneously with an external filling liquid, and no longer with the patient's blood as is the case with the traditional equipment. Similarly, the removal of bubbles from the cannula or cannulae is carried out simultaneously with the removal of bubbles from the arterial and venous lines, since the assembly arterial line+arterial cannula or cannulae+where appropriate, venous cannula or cannulae+venous line constitute a closed circuit from which bubbles are very readily removed by means of the heart-lung machine.

Moreover, the proximal seating of each cannula can be attached to the line at the outset in an especially resistant manner, as a result of industrial means (sticking, crimping, improved links, special nuts, and the like). Lastly, according to a preferred embodiment of the invention, this improved connecting device can be packaged in a multi-stage packing system which enables the portion of the circuit to be kept "sterile" at each stage of its use. In particular, this packaging system comprises a packing which enables the portion of the circuit intended for the operative field (distal portion of the arterial and venous lines and all of the arterial cannula or cannulae and, where appropriate, of the venous cannula or cannulae) to be kept "sterile", while the other portion (the proximal sections of these lines) can be connected by the perfusionist to the heart-lung machine. This latter preferred embodiment of the invention permits a significant gain in time for the surgeon, in particular in the case of an emergency where the patient must be operated on with the minimum of delay. In effect, as a result of this multi-stage packing system, the perfusionist can, at his level of the procedure, start up the extracorporeal circulation equipment, in particular carry out the filling of the arteriovenous shunt and the removal of bubbles therefrom. In parallel with this treatment by the perfusionist, the surgeon can begin the surgical operation and, when exactly the right moment is reached, introduce the arterial cannula or cannulae into the artery or arteries and, where appropriate, the venous cannula or cannulae into the appropriate vessel or vessels. The surgeon no longer has to wait for the arterial line and the venous line to be filled and the bubbles removed; he no longer has to fill the intravascular cannula or can-nulae, he no longer has to remove the bubbles therefrom, he no longer has to connect them to the corresponding lines, he longer has to attach them with special links or other means of attachment, and lastly, he no longer has to carry out the final operation of removing bubbles from the section cannula seating/-distal end of the line. Moreover, the operations of clamping and unclamping are halved. In summary, the device according to the invention simplifies in the extreme the manipulations by the surgeon: the latter has only to introduce the cannula or cannulae into the vessel or vessels of the patient after taking off the distal linking member.

Other characteristics and advantages of the invention will emerge from the detailed description which follows of some of its embodiments. For this purpose, reference will be made to the attached drawing, wherein:

FIG. 5 shows a device according to the invention in its packing;

FIG. 6 shows this same device in a variant of packing, and

FIG. 7 is a sectional view according to the line 7—7 of FIG. 6.

Figure 1:
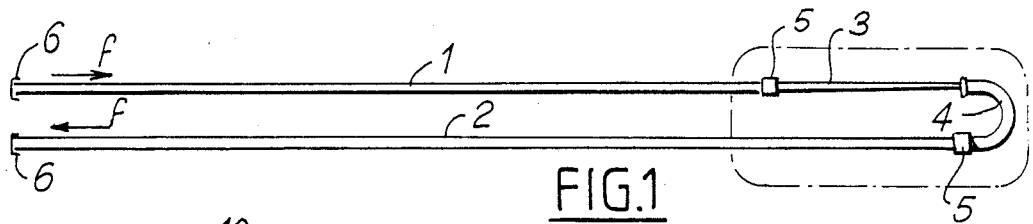
FIG. 1 is a plan view of one of the embodiments of the connecting device according to the invention.

The connecting device shown in FIG. 1 comprises an arterial line 1 whose distal end is connected to an arterial cannula 3 which is itself connected at its distal end to a linking member 4 composed of a U-shaped hollow sleeve connected to a venous line 2. The linkages arterial line 1/arterial cannula 3 and venous line 2/linking member 4 are provided by simple one-way connectors 5. The proximal ends of the lines are preferably protected by caps 6 which the perfusionist will have to take off to attach the device to the heart-lung machine. Once this connection has been made, thereby looping-in the arteriovenous shunt, the latter is filled with a filling liquid (solution, external blood, and the like) which will be propelled in the direction of the arrows f: outflow through the arterial line 1, return through the venous line 2. After the time required by the operation of recirculation of the filling liquid, which is necessary for the complete removal of bubbles from the shunt, the surgeon, after clamping the lines 1 and 2, will have to take off the linking member 4 and then simply introduce the arterial cannula 3 into the patient's artery, and he will, moreover, have to connect the venous cannula or cannulae to the distal end of the venous line. After the lines 1 and 2 have been unclamped, the patient will be installed in extracorporeal circulation.

Figure 2:
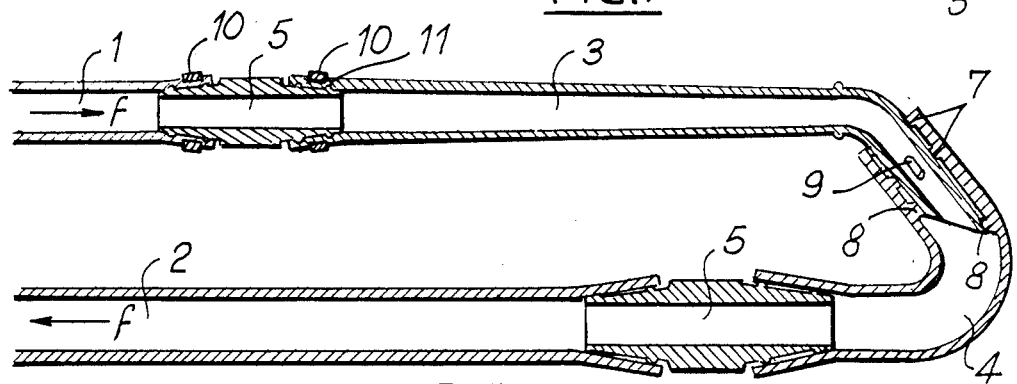
FIG. 2 is a sectional view, on a larger scale, of the distal portion of a device such as that of FIG. 1.

FIG. 2 shows, in section, the distal portion of the shunt enclosed with a chain-dotted line in FIG. 1. In this figure, the arterial cannula 3 contains a small variant: its distal end is tilted with respect to its principle axis. Moreover, it contains one or more lateral holes 9. The linking member 4 is V-shaped and not U-shaped to take account of the shape of the distal end of the cannula. This figure demonstrates the detail of the connectors 5, which preferable contain sealing segments 11 enabling very firm attachment of the line 1, the cannula 3, the sleeve 4 and the line 2 to be achieved. The connection points of the line 1 and the cannula 3 are reinforced by the presence of two attachment links 10.

As regards the linking member 4, the latter contains circular sealing segments 7, as well as another sealing segment 8 of approximately elliptical shape, avoiding any risk of a dead space at the distal end of the cannula 3, in which space air bubbles might stagnate.

According to another embodiment of the invention, not shown but readily deducible from the embodiment of FIG. 1 or 2, the venous line 2 can be directly connected to a venous cannula via, where appropriate, the connector 5: in this case, the proximal seating of the venous cannula is connected to the connector 5 of the venous line, whereas its distal end is connected to the linking member 4.

Figure 3:
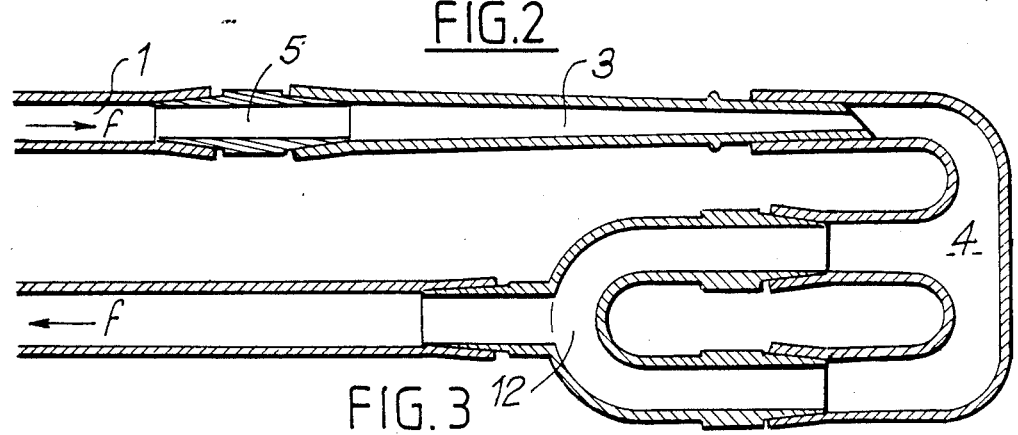
FIG. 3 is a view similar to FIG. 2 of another embodiment.

FIG. 3 shows a variant in which the one-way connector 5 of the venous line 2 has been replaced by a three-entry connector 12, connected to a linking member 4 which itself has three entries. With such an arrangement, the surgeon can connect two venous cannulae directly to the two parallel or Y- shaped branches of the connector 12.

Figure 4:
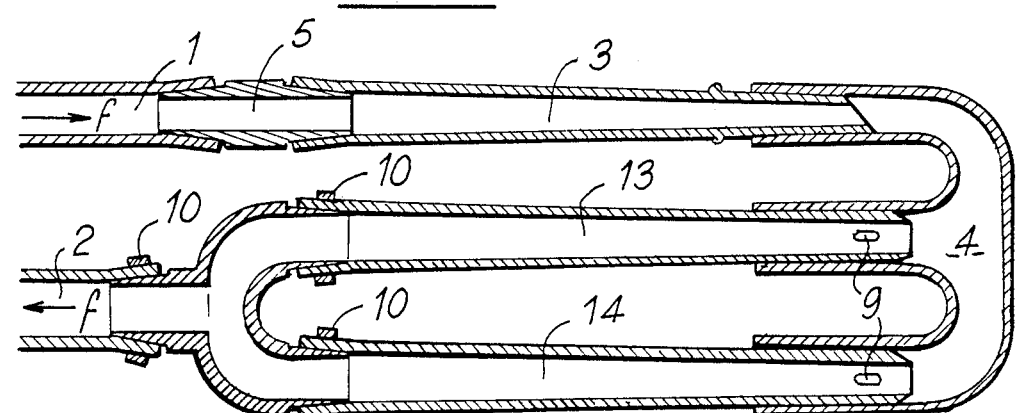
FIG. 4 is a view similar to FIG. 2 of another variant.

FIG. 4 shows a variant of the embodiment of FIG. 3, in which two venous cannulae 13 and 14 are mounted. These two cannulae can contain, additionally, lateral holes 9. Moreover, they can be securely united with the connector 12 by sticking, by nuts, by clamping links 10 or by the other means.

FIG. 5 shows a connecting device according to the invention, which is packaged in at least two packings which provide for the sterility of the assembly until the final use of the device by the surgeon.

In this system, when the external packing 16 is removed, the internal packing 15, kept sterile, can be introduced into the surgical unit, or even arranged as it is on the operative field. Only after the packing 15 has been opened will the surgeon be able to pass the perfusionist the proximal ends of the lines 1 and 2, protected by caps 6 whereas he will keep on the operative field the distal portion of the device containing the arterial cannula 3.

FIG. 6 shows a device according to the invention, packaged in a system of three multi-stage packings, according to a preferred embodiment of the invention.

These three multi-stage packings preserve the complete or partial sterility of the arteriovenous shunt at every stage of its use, and are designated overall, from the inside outwards, A, B and C.

The inner packing A, which is accessible after opening the intermediate packing B, is advantageously, as shown, a simple trough or tray without a lid, on which are coiled the ends of the lines 1 and 2 intended for the operative field with the cannula 3 and the sleeve 4.

The intermediate packing B, which is accessible after opening the outer packing C, is advantageously, as shown, a trough incorporating a removable seal 25 (see FIG. 7) through which pass the arterial line 1 and venous line 2 emerging from the packing A through a notch 26. Seal 25 is itself a friction fit in a socket 27 in the trough B. The seal 25 is made in an elastomeric material such as polyethylene foam, polyester foam or polyurethane foam, rubber or silicone, or any other material which enables the seal to conform well to its housing 27 and ensures that the seal is fixed in the latter by clamping. The trough B is closed by a lid 30, which preferably takes the form of a transparent peelable film attached by welding or sticking to the periphery of the trough and detachable by means of a tab 31.

The outer packing C, which accommodates the portions of the lines 1 and 2 which can be connected to the heart-lung machine, is shown in the form of a trough sealed over its top by a lid or peelable film 32 with an opening tab 33. The proximal ends of the lines are protected by caps 6. The packing C can, however, be any other packaging device which enables the sterility of its contents to be completely protected, such as a closed bag impermeable to bacteria.

The time sequence of taking and opening these three packings and the use of the equipment according to the invention are as follows:

(1) taking and opening of the outer packing C by the perfusionist;

(2) taking, by the perfusionist, of the portion of the arterial line 1 and venous line 2 which emerges from the packing B, followed by connection of the proximal ends of these lines, after removal of the protective caps 6, to the heart-lung machine;

(3) filling of the arteriovenous shunt and removal of bubbles therefrom. During this operation, a portion of the arteriovenous shunt intended for the operative field in its packing A is always kept completely sterile, enclosed in the packing B in a manner impermeable to external contamination by virtue of the seal 25 and the lid 30.

Moreover, the lid 30, which is preferably transparent, enables it to be verified that no bubbles remain in the arteriovenous shunt at the end of the bubble removal operation;

(4) opening of the intermediate packing B by removing the lid 30. This opening, carried out by the perfusionist or another of the surgeon's assistants, is carried out without the need for aseptic conditions, in particular in the case of a lid in the form of a peelable film equipped with a tab 31;

(5) taking of the packing A by the surgeon or his assistant equipped with sterile gloves, and then removal of the sterile portion of the arteriovenous shunt intended for the operative field, without the need for aseptic conditions; even if the arteriovenous shunt touches the outer edge of the packing A, since the latter has been kept completely sterile, there is no possibility of contamination of the said shunt;

(6) after clamping of the lines, breaking of the arteriovenous shunt by the surgeon, who disconnects the arterial line 1 with its cannula 3 from the venous line 2, followed by the introduction, by the surgeon, of the arterial cannula into the patient's artery and the connection of the venous cannula (or the two venous cannulae) to the distal end of the venous line 2, when these cannulae, as is the case for the device illustrated in FIGS. 6 and 7, are not already incorporated therein.

The patient can then be installed in extra-corporeal circulation after unclamping the lines.

It should be noted that the sterility packaging systems shown in FIGS. 5, 6 and 7 are given by way of illustration and without implied limitation, and the same applies to the variant of device shown in these figures. In effect, these packaging systems can contain other embodiments of the device according to the invention, such as a device with a three-entry connector for double venous cannulation, or comprising one or two venous cannula or cannulae in addition to the arterial cannula. Similarly, the device according to the invention can include a prebypass filter, and the multi-stage packing system can package, in addition to the device according to the invention, suction and/or cardioplegia and/or left discharge lines, or other lines.

The device according to the invention is intended especially for installing in extracorporeal circulation patients undergoing open-heart surgery, or who require extracorporeal oxygenation of one or more parts of their body.

I claim:

1. A connecting device for a circuit for extracorporeal circulation of a patient's blood through a heart-lung machine or the like, comprising:

an arterial line and a venuous line whose linkage with each other and in a closed circuit to an associated heart-lung machine forms an arterio-venuous shunt, at least one arterial cannula connected to the arterial line and connected detachably at its distal end to the venuous line, and a package enclosing the arterial and venuous lines and the at least one arterial cannula in a sterile manner, the package comprising:

a first, inner, packing which contains the portion of the shunt intended for the operative field, including the at least one arterial cannula, a second intermediate, packing which encloses the first packing and forms, from the standpoint of sterility, a screen between the first packing and a third outer packing.

the third packing containing said second packing and a remaining portion of the arterial and venuous lines which are intended to be connected to the associated heart-lung machine.

2. The device as claimed in claim 1, wherein a Y-shaped connector is mounted on the distal end of the venous line and the detachable linkage is provided by a three-entry member, one of which entries is engaged on the arterial cannula and the other two on the two free entries of the connector or on the distal ends of two venous cannulae mounted, respectively on these two entries of the connector.

3. The device as claimed in claim 1, wherein the intermediate packing contains at least one passage for the remaining portion of the arterial and venuous lines which are intended to be connected to the associated heart-lung machine, while protecting the sterility of a portion of the arterial and venuous lines intended for the operative field.

4. A connecting device for a circuit for extracorporeal circulation of a patient's blood through a heart-lung machine or the like, comprising:

an arterial line and a venuous line whose linkage with each other and in a closed circuit to an associated heart-lung machine forms an arterio-venuous shunt, at least one arterial cannula connected to the arterial line and detachably connected at its distal end to the venuous line, An alternately detachable and engageable linking member including a hollow elastic substantially U-shaped sleeve for linking a distal end of the at least one arterial cannula with the venuous line said sleeve being engaged at one end of the arterial cannula and connected at its other end to the venuous line.

5. The device as claimed in claim 2, wherein said detachable linking member contains, at least on its arterial portion, at least one sealing segment.

6. The device as claimed in claim 5, wherein the sealing segment is circular.

7. The device as claimed in claim 5 wherein the sealing segment is of an approximately elliptical configuration.

8. The device of claim 5 wherein the sealing segment includes an inwardly facing rib located on an inner face of the sleeve.

9. The device as claimed in claim 2 further comprising a connector mounted between said venuous line and said linking member.

10. The device as claimed in claim 2 further comprising a hollow connector for connecting the distal end of the aterial line to a proximal seating of the arterial cannula.

11. The device of claim 10 wherein the connector includes a pair of outwardly facing sealing ribs for sealing, respectively, against an inner surface of the arterial cannula and an inner surface of the arterial line.

12. The device of claim 10 further comprising a clamping band for securing one of the arterial cannula and the arterial line to the connector.

13. The device as claimed in claim 6, wherein the attachment of the proximal seating of said arterial cannula to the distal end of the connector is provided by a clamping link.

14. The device of claim 13 wherein the clamping link includes a band.

* * * * *